United States Patent [19]

Manning

[11] Patent Number: 4,469,911

[45] Date of Patent: Sep. 4, 1984

[54] ISOBUTENE REMOVAL FROM C4 STREAMS

[75] Inventor: Harold E. Manning, Houston, Tex.

[73] Assignee: Petro Tex Chemical Corporation, Houston, Tex.

[21] Appl. No.: 439,735

[22] Filed: Nov. 8, 1982

Related U.S. Application Data

[63] Continuation of Ser. No. 199,839, Oct. 23, 1980, abandoned.

[51] Int. Cl.$^3$ .............................. C07C 2/24; C07C 2/02
[52] U.S. Cl. ....................................... 585/515; 585/526
[58] Field of Search ................................ 585/515, 526

[56]  References Cited

U.S. PATENT DOCUMENTS

| | | | |
|---|---|---|---|
| 2,593,417 | 4/1952 | D'Alelio | 260/669 |
| 3,037,052 | 5/1962 | Bortnick | 260/485 |
| 3,326,866 | 6/1967 | Haag | 260/79.3 |
| 3,370,101 | 2/1968 | Hayes et al. | 260/671 |
| 3,518,323 | 6/1970 | Pine et al. | 260/683.15 |
| 3,531,539 | 9/1970 | Tidwell | 260/677 |
| 3,546,317 | 12/1970 | Gislon et al. | 260/683.15 |
| 3,629,478 | 12/1971 | Haunschild | 260/677 A |
| 3,823,198 | 7/1974 | Goldsby | 260/677 |
| 3,832,418 | 8/1974 | Bercik et al. | 260/683.15 R |
| 4,039,590 | 8/1977 | Ancillotti et al. | 260/614 |
| 4,065,512 | 12/1977 | Cares | 260/641 |
| 4,100,220 | 7/1978 | Bowman et al. | 260/683.15 R |
| 4,198,530 | 4/1980 | Wentzheimer | 568/697 |
| 4,215,011 | 7/1980 | Smith | 585/515 UX |
| 4,232,177 | 11/1980 | Smith | 585/324 |
| 4,242,530 | 12/1980 | Smith | 585/515 X |

FOREIGN PATENT DOCUMENTS

| | | | |
|---|---|---|---|
| 907429 | 10/1962 | United Kingdom | 585/515 UX |
| 956357 | 4/1964 | United Kingdom | 585/515 UX |
| 959756 | 6/1964 | United Kingdom | 585/515 |
| 973555 | 10/1964 | United Kingdom | 585/515 |
| 1045210 | 10/1966 | United Kingdom | 585/515 |
| 1143971 | 2/1969 | United Kingdom | 585/515 |
| 1171950 | 11/1969 | United Kingdom | 585/515 |
| 1171970 | 11/1969 | United Kingdom | 585/515 |

OTHER PUBLICATIONS

W. O. Haag, Kinetics and Catalysis No. 73, vol. 63, pp. 140-147.

Primary Examiner—Paul F. Shaver
Attorney, Agent, or Firm—Kenneth H. Johnson

[57]  ABSTRACT

The isobutene in C4 hydrocarbon streams containing 5 to 60 mole % isobutene and n-butenes may be reduced to a level of 0.2 mole % or less by passing the feed stream at LHSV 0.5 to 12 in liquid phase through a fixed bed cation exchange resin catalyst in a tubular reactor with a water heat exchange medium maintained at a temperature of 30° to 80° C., whereby the isobutene is oligomerized and easily separated from the remaining C4 by fractionation.

13 Claims, 3 Drawing Figures

ISOBUTENE REMOVAL FROM C₄ STREAMS

This is a continuation of application Ser. No. 199,839 filed Oct. 23, 1980 now abandoned.

BACKGROUND OF THE INVENTION

1. Field of the Invention

The present invention relates to the separation of isoolefins from streams containing mixtures of an isoolefin and the corresponding normal olefin. The present invention is especially useful for the separation of isobutene from streams containing n-butenes.

2. Prior Art

Isoolefins of four carbon atoms are difficult to separate from the corresponding normal olefin by simple fractionation because of the closeness of their boiling points. In prior art processes as generally practiced commercially, the isoolefin is selectively absorbed by sulfuric acid and the resulting isoolefin-containing sulfuric acid extract is then diluted and heated or treated with steam to separate the isoolefin.

Isobutene and diisobutene are of significant value, having diverse applications. For example, isobutene is one of the comonomers for butyl rubber and diisobutene is an intermediate in the preparation of detergents. The isobutene oligomers are useful as polymer gasoline. The n-butenes are required in pure form for homopolymerization and as feeds for the oxidative production of butadiene. One manner of separating these components is to pass the mixture through a cold acid extraction procedure wherein the stream is fed into a bath of concentrated sulfuric acid. Separation is achieved by virtue of the solubility of the isobutene in the sulfuric acid, the n-butenes and other hydrocarbons present passing overhead, for example as shown in U.S. Pat. Nos. 3,546,317 and 3,823,198.

Other processes have used various catalysts for converting the isobutene to diisobutene which is then easily separated from the product stream. For example, a process using a molecular sieve and elevated temperatures is disclosed in U.S. Pat. No. 3,531,539; U.S. Pat. No. 3,518,323 employs a supported nickel oxide catalyst; and U.S. Pat. No. 3,832,418 employs a Group VI or VIII metal deposited on acidic, amorphous silica-alumina in the same manner.

More recently, U.S. Pat. No. 4,215,011 disclosed the use of acid cation exchange resin in a heterogenous combination reaction-distillation system for the selective dimerization of isobutene in the presence of normal butenes.

Although the present process is suited to treat other isoolefin-normal olefins mixtures, it is of particular significance for the recovery of product streams with sufficiently low levels of isobutene to be processable to obtain useable n-butenes and particularly butene-1 which is the n-butene isomer employed in homopolymerization to produce polybutene or copolymerization with other monomers and as the preferred feed for oxidative dehydrogenation to produce butadiene-1,3.

It is a principal feature of the present process that the amount of isobutene in the stream is reduced to levels sufficiently low to allow further separation of a useful butene-1 product. It is another feature of the present process that a very useful product is produced from the isobutene, i.e., polymer gasoline. It is a particular advantage of the present process that it may be operated to obtain the above results with a limited loss of butene-1.

It is a further advantage of the present process that the diisobutylene product produced according to the present process may have lower ratios of codimer (the reaction product of n-butenes and isobutene) and triisobutene to diisobutene than the prior cold acid method of removing isobutene from C₄ streams.

Another feature of the present process is the substantial energy saving over the cold acid method of isobutene removal and a deduction in capital expenditures to replace and/or repair processing equipment that has failed due to the corrosive nature of the sulfuric acid.

SUMMARY OF THE INVENTION

The present invention is a process for removing isobutene from a feed stream comprising predominately C₄ hydrocarbons and containing isobutene and n-butenes, said isobutene being present in an amount of from 5 to 60 mole percent comprising:

(a) contacting said feed stream in liquid phase with a fixed bed cation exchange resin in a reactor at a temperature in the range of from 30° to 80° C., preferably a lower temperature of 40° C. and an upper temperature of 60° C., said feed stream being fed at a rate of a liquid hourly space velocity of from about 0.5 to 12, preferably at least 2.5. (Temperatures of up to 100° C. may be used, if the isomerization or reaction of normal butenes is not a consideration. Furthermore, the isobutene is the most reactive C₄ olefin and will preferentially react. Hence, the higher the mole % of isobutene, the less likely is the n-butene to oligomerize. However, even high concentrations of isobutene require lower temperatures to obtain the desired dimer product preferentially);

(b) reacting the isobutene to form oligomers thereof having number average molecular weight of C₁₆ hydrocarbons or less to form a product stream comprising said C₄ hydrocarbons and oligomers and having a substantially lower amount of isobutene than said feed stream and;

(c) removing said product stream from said reactor.

The product stream thus produced is then processed further in a preferred embodiment by fractionating said product stream to recover an overhead C₄ fraction having an isobutene content substantially lower than said feed stream and a bottoms fraction consisting essentially of said oligomers.

In one embodiment the present invention is a process for recovering a product stream having less than 0.2 volume percent of isobutene therein from a feed stream as defined and containing at least 50 percent of the butene-1 of said feed stream and more preferably at least 80 percent of the butene-1 of the original feed stream. The present invention is also a method for producing diisobutylene from the defined feed.

In other embodiments, the production is isobutene oligomer, particularly the diisobutene is the desired result and the production of a very low isobutene content stream or the loss of butene-1 are not prime considerations.

The conditions of space velocity and temperature are adjusted within the ranges specified to obtain maximum isobutene removal and minimal loss of butene-1 by isomerization or the loss of normal butenes by reaction.

One means of maintaining the temperature in said reaction is by having a heat exchange medium associated therewith.

DETAILED DESCRIPTION OF THE INVENTION AND PREFERRED EMBODIMENTS

Figure 1:
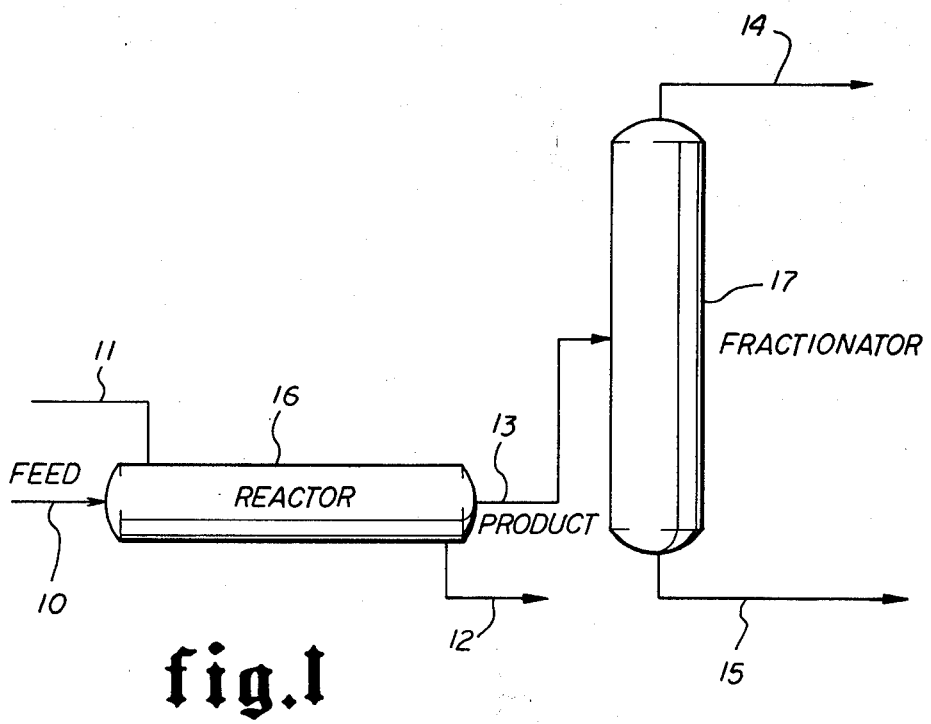
FIG. 1 is a schematic depiction of a preferred embodiment of the present process.

The principal consideration in treating a $C_4$ stream containing isobutene, butene-1, butene-2, normal butane and isobutane in the present process is the removal of isobutene therefrom. Complete removal would be most desirable. However, in practice that is not possible without serious detriment to the remainder of the feed stream. Hence, in one embodiment, an overhead $C_4$ fraction containing less than 0.2 mole percent of isobutene is that determined to be suitable for further processing to produce a useable butene-1 fraction.

The $C_4$ feed streams may have small amounts of $C_3$ and $C_5$. However, these are usually less than 1.0 volume percent of the total stream and are of no consequence. Further the degree of skill employed in operating refineries now makes possible $C_4$ streams substantially free of lower and higher hydrocarbons.

In carrying out the present process, it was determined that the temperature of cooling medium (which reflects the exotherm in the catalyst bed) was of particular importance. It was found that operating the process at temperatures below about 50° C., e.g., 40° C. failed to reduce the isobutene content to the 0.2 volume percent or less, for more than a few days on stream, even at longer residence times. An advantage of lower temperatures, e.g., 30° to 40° C. is a very favorable ratio, that is, low ratio isobutene-n-butene codimer and triisobutene to diisobutene. Higher temperatures favor the cooglimerization of the isobutene. The temperature range of 40° to 60° C. reflects the operable range which may be used to carry out the reaction without undue loss of n-butene over a useful time trend of the catalyst which tends to decline in activity, as higher polymers are deposited thereon. That is, with a fresh catalyst, as low a temperature as possible would be maintained until a decline in the isobutene removal required higher temperatures.

As stated, in one embodiment the primary purpose of the present process is the removal of isobutene from the feed stream to the 0.2 or less mole percent level. However, higher temperatures than required for this are detrimental in that they favor loss of the desired butene-1 by (1) isomerization to butene-2, (2) copolymerization with the isobutene and/or (3) polymerization of the n-butenes. Thus, the operation of the present process at any higher temperature within the recited range than necessary to reduce the isobutene content below 0.2 vol. % is counter productive to the butene-1 content thereof. The determination of the upper operating temperature is readily made by the operation of the process and routine sampling based on the extent the operator is willing to sacrifice butene-1 for isobutene removal. Beyond the upper limit of 100° C., even with the reduced activity of the catalyst, the rate of butene-1 loss, e.g., by isomerization would be very high. When the desired purpose of the process is the production of the isobutene polymer, then an upper temperature of 100° C is acceptable. The isobutene oligomer product is principally dimer and trimer, with some tetramer; and codimers with n-butenes. However, the dimer (diisobutene) is the predominate product. Also at higher temperatures the normal butenes react not only with isobutene but with each other to form dimers and higher oligomers.

The deactivated catalyst is not lost and is easily returned to its original level of activity (allowing for some loss in activity as experienced with all catalysts regardless of regeneration treatment) by removing the built up polymer. This is achieved by discontinuing the $C_4$ feed and passing a solvent for the oligomer through the reactor. Any of the conventional solvents for thermoplastic hydrocarbon-polymers may be used, so long as they are not activated by the resin catalyst. For example, the various hydrocarbons, including, butane, pentane, hexane, benzene, toluene, xylene and the like may be used. Diisobutylene and the oligomers from the reaction are also useful and completely non-contaminating for this purpose. The solvents are employed with the heat exchange medium used to lower the temperature, for example to around 40° C. for a determinable period during which the solvent in liquid phase is passed through the fixed bed of resin. The feed stream is reinstituted after the operator determines the polymer is sufficiently removed.

The isomerization of butene-1 was found to be effected by the residence time of the feed stream in the catalyst bed. For example, at a temperature of about 60° C (fresh catalyst) a reduction of the isobutene content in the product stream of 0.2 vol. % or less is still obtainable with only about 10% loss in butene-1 at LHSV 12.

Catalysts suitable for the new process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization along or in admixture with other monovinyl compounds, or by crosslinking with polyvinyl compounds; for example, with divinyl benzenes, divinyl toluenes, divinylphenylethers and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C., and the sulfuric acid should contain unreacted sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Patent Specification No. 908,247).

The ion exchange resin is preferably used in a granular size of about 0.25 to 1 mm, although particles from 0.15 mm up to about 2 mm may be employed. The finer catalysts provide high surface area, but also result in high pressure drops through the reactor. The macroreticular form of these catalysts is preferred because of the much larger surface area exposed and the limited swelling which all of these resins undergo in a nonaqueous hydrocarbon medium. Preferred catalysts have surface areas of from about 20 to 600 square meters per gram.

Referring to FIG. 1, a schematic representation of a preferred embodiment of the present process is shown. The isobutene containing $C_4$ feedstream enters reactor 16 via line 10 where it is contacted with the resin catalyst (not shown). The reaction temperature is maintained constant by means of a fluid medium entering the reactor through line 11 where it is in indirect contact with the catalysts to either remove heat or supply heat, such as on start-up. The fluid medium exits the reactor via line 12 and is treated elsewhere as required to maintain the desired temperature in the reactor.

The fluid medium can be any fluid capable of providing indirect heat exchange with the fixed bed catalyst. Water is particularly preferred because of the operational temperature range for the present process. However, air or organic liquids could be employed for this purpose.

In the reactor the $C_4$ stream contacts the catalyst and isobutene is preferentially reacted with itself to form a mixture of dimers, trimers and tetramers of number average molecular weight of a $C_{16}$ hydrocarbon or less. This product passes via line 13 into fractionator 17 where by simple distillation the product is split to recover the oligomer as a bottoms fraction removed through line 14 and the $C_4$'s as an overhead, removed through line 15, hence to further treatment for further separation of the remaining $C_4$'s.

Figure 2:
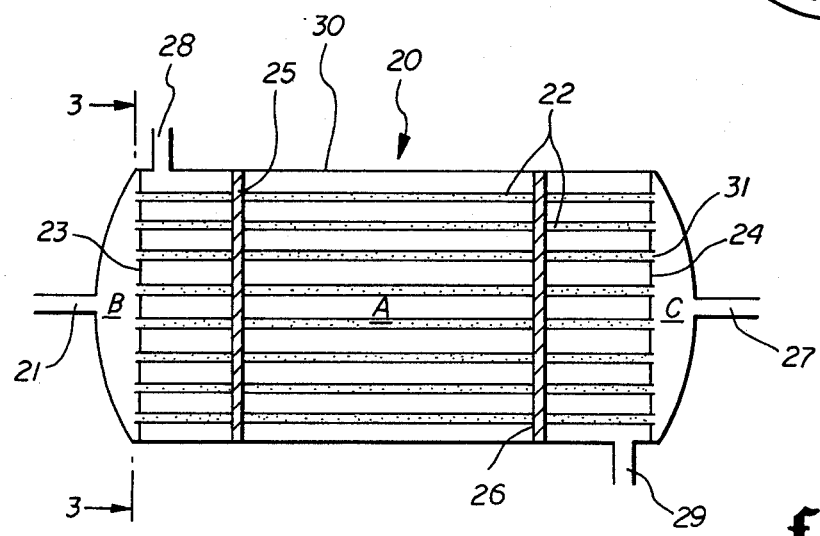
FIG. 2 is a cross sectional elevation of a reactor for carrying out the process of the present invention.

The heat exchange fluid is in indirect contact with the fixed catalyst bed. FIG. 2 shows a conventional and preferred means of obtaining this contact. Reactor 20 is a multitube reactor comprising a shell 30 having mounted therein tubes 22, usually of ⅛ to 2 inches outside diameter. The reactor is shown horizontally, however it could be vertical or inclined. The tubes 22 are mounted through plates 25 and 26 respectively and attached at each end to header plates 23 and 24 which are to prevent fluid communication between the area adjacent to the tubes A, the feed entry area B, and product exit area C. The tubes 22 are in liquid communication with areas B and C. A feed entry pipe 21 is located on the B area and a product exit pipe 27 is located on the C area. Heat exchange medium is provided into the A area via pipe 28 and an exit is provided via pipe 29.

Figure 3:
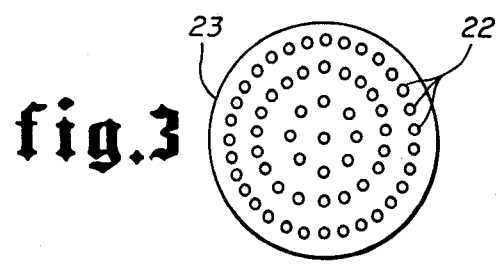
FIG. 3 is a cross sectional view of the reactor of FIG. 2 taken along line 3—3.

The tubes 22 are packed with the cation exchange resin in granular form 31 and means such as screen (not shown) are fitted to each tube to retain the catalyst therein. FIG. 3 shows an arrangement of tubes 22 in header plate 23.

The reaction of isobutene with itself is exothermic and the heat exchange medium, e.g., water provides the means for controlling the reaction to favor a selective reaction of isobutene with itself to form oligomers, rather than the production of cooligomers with the n-butenes or higher polymers, i.e., a runaway reaction in the absence of such control.

The reaction is carried on in liquid phase and sufficient pressure is maintained on the system to keep the $C_4$ stream in liquid phase under the conditions of reaction, i.e., about 35 to 300 psig.

The term liquid hourly space velocity (LHSV) means the liquid volumes of hydrocarbon per volume of reactor containing catalyst per hour.

The $C_4$ feed stream should be free or substantially free of contaminates such catalyst poisons, such as metal cations or basic nitrogen compounds, e.g., $NH_3$ or dimethylamine. Water or methanol may be present in small amounts, insufficient to form an entrained second phase, to serve as a catalyst modifier.

EXAMPLES

In the following examples, the reactor consisted of a preheat section of coiled ⅛" OD stainless steel tubing connected to ¼" OD stainless steel tubing packed with 25 cc of dry resin as described. Both sections were immersed in a water bath of controlled temperature which is the temperature reported. A back-pressure regulator located downstream of the catalyst bed was used to maintain the desired pressure in the reactor system. Product effluent was collected in a stainless steel vessel, downstream of the pressure regulator. After a sufficient volume of effluent had been collected for analysis, the contents of the SS vessel were transferred to a tared and evacuated Pyrex bottle fitted with a rubber septum mounted in a perforated metal cap. A 20-gauge needle attached to the SS vessel was inserted through the rubber septum of the bottle and the reaction products were collected for reweighting. The contents of the Pyrex bottle were then evaporated at room temperature and later at 90° F. via a transfer line into a second evacuated bottle immersed in a mixture of acetone and solid $CO_2$. Separation of the lower boiling, unreacted $C_4$ hydrocarbons from the higher boiling oligomerized products was thus effected and the weight percent of oligomers calculated. The composition of each of the two hydrocarbon fractions was determined chromatographically.

The following abbreviations are used in the examples;

| Propylene | = | $C_3^=$ |
| Isobutane | = | i-$C_4$ |
| Normal-butane | = | n-$C_4$ |
| Butene-1 | = | B-1 |
| Butene-2 | = | B-2 |
| Butene-2(trans) | = | B-2-t |
| Butene-2(cis) | = | B-2-c |
| Isobutene | = | i-$C_4^=$ |
| Butadiene | = | Bd |
| Liquid volume | = | LV |
| Dimer I | = | 2,4,4-trimethyl-pentene-1 |
| Dimer II | = | 2,4,4-trimethyl-pentene-2 |

EXAMPLE 1

The catalyst employed was Amberlyst 15 (Rohm and Haas Co.) which is a sulfonated copolymer of styrene and divinyl benzene having a porosity of 32% and surface area of 45 square meters per gram. The conditions, feed analysis and product analysis are reported in TABLE I.

TABLE I

| Reaction Conditions | Temperature | 60° C. | | | | | |
|---|---|---|---|---|---|---|---|
| | Pressure | 100 psig | | | | | |
| | LHSV | 5.0 | | | | | |

| Stream Analyzed | C₄ Analysis (Mol %) | | | | | | Oligomer Yield, Wt. % of Feed |
|---|---|---|---|---|---|---|---|
| | $C_3^=$ | i-$C_4$ | n-$C_4$ | B-1 | i-$C_4^=$ | B-2's | Bd. |
| Feed | 0.3 | 2.3 | 8.7 | 16.7 | 51.2 | 20.3 | 0.4 | — |
| Product | 0.2 | 5.2 | 19.5 | 21.4 | <0.1 | 53.6 | <0.1 | 57.1 |

EXAMPLE 2

This run was conducted at 2.5 LHSV at low temperature. Even at this long residence time, the low temperatures were still only effective for a short period. The conditions and results are reported in TABLE II.

TABLE II

Catalyst[1]: Amberlyst 15
Conditions: LHSV = 2.5, Pressure = 100 psig.
Feed: C₄ Hydrocarbons from Plant with additional i-$C_4^=$.

| Reaction Temp, °C. | Hrs. on Stream | C₄ Product Analysis (Chromatographic %)[2] | | | | | |
|---|---|---|---|---|---|---|---|
| | | i-$C_4$ | n-$C_4$ | B-1 | i-$C_4^=$ | B-2-t | B-2-c |
| — | Feed Analysis | 0.01 | 4.85 | 83.18 | 7.36 | 4.37 | 0.25 |
| 40 | 58 | 0.04 | 5.04 | 82.60 | —[3] | 7.73 | 4.58 |
| 40 | 79 | 0.06 | 5.04 | 82.43 | — | 7.72 | 4.70 |
| 30 | 81 | 0.02 | 4.87 | 86.82 | 1.47 | 5.36 | 1.45 |
| 30 | 103 | 0.02 | 4.70 | 85.96 | 3.56 | 4.76 | 0.89 |
| 40 | 105 | — | 4.91 | 85.19 | 0.43 | 6.59 | 2.88 |
| 40 | 108 | 0.04 | 4.99 | 84.19 | 0.46 | 6.93 | 3.36 |
| 40 | 131 | 0.04 | 4.79 | 84.76 | 2.47 | 5.86 | 2.08 |

[1]Wet resin washed with acetone and dried before loading into reactor.
[2]Results are approximate LV %.
[3]No detectable conc. of i-$C_4^=$.

EXAMPLE 3

Several resin catalysts were evaluated over a range of temperatures in the reactor described. The reactor pressure was 100 psig, LHSV 5. The feed had the following analysis:

| | mole % |
|---|---|
| $C_3^=$ | 0.29 |
| i-$C_4$ | 2.30 |
| n-C | 8.73 |
| B-1 | 16.72 |
| i-$C_4^=$ | 51.18 |
| B-2-t | 15.11 |
| B-2-c | 5.16 |
| Bd | 0.44 |

The results are reported in TABLE III and show at low temperatures the ratio of codimer and triisobutene to diisobutene. A typical commercial cold acid plant analysis using a similar feed was shown as follows:

| | LV % |
|---|---|
| Diisobutene | 73 |
| Codimer | 6 |
| Trimer | 21 |

TABLE III

| Catalyst | Product | 30° C. | 40° C. | 50° C. | 60° C. |
|---|---|---|---|---|---|
| | | Isobutylene Conversion, Wt. % | | | |
| Amberlyst XN 1010 | | 62.1 | 90.6 | 99.8 | 100.0 |
| Amberlyst 15 | | 35.7 | 86.9 | 98.6 | 100.0 |
| Lewatit SPC 118 | | 44.9 | 86.3 | 98.0 | 100.0 |
| | | Product Composition LV % | | | |
| Amberlyst XN1010[1] | Dimer I | 68.4 | 55.8 | — | 35.8 |
| | Dimer II | 17.8 | 16.3 | — | 11.8 |
| diisobutene | | | | | |
| Codimer | | 0.9 | 1.6 | — | 1.5 |
| Trimer | | 12.9 | 26.9 | — | 50.3 |
| Amberlyst 15 (CSP)[2] | Dimer I | 63.6 | 56.3 | 32.5 | 28.5 |
| | Dimer II | 18.8 | 17.7 | 11.0 | 10.2 |
| diisobutene | | | | | |
| Codimer | | 3.9 | 3.7 | 8.5 | 11.1 |
| Trimer | | 13.8 | 22.3 | 48.0 | 50.1 |
| Lewatit SPC 118[3] | Dimer I | 64.8 | 60.2 | 40.3 | 43.1 |
| | Dimer II | 18.0 | 17.2 | 12.4 | 13.5 |
| diisobutene | | | | | |
| Codimer | | 2.1 | 4.0 | 4.7 | 7.4 |
| Trimer | | 15.1 | 18.5 | 42.6 | 36.0 |

[1]Rohm and Haas
[2]Rohm and Haas
[3]Bayer

An expanded examination of the process using Rohm and Haas XN-1010 was carried out at various temperatures and flow rates using the reactor as described at 100 psig. The results which are reported in TABLE IV show the same relation to flow rate as those of example 3, that is, temperature is a more important consideration in maintaining low codimer and trimer production.

TABLE IV

| Run No. | 1 | 2 | 3 | 4 | 5 | 6 | 7 | 8 | 9 | 10 | 11 | 12 |
|---|---|---|---|---|---|---|---|---|---|---|---|---|
| Reaction Temperature, °C. | 30 | 30 | 30 | 40 | 40 | 40 | 50 | 50 | 50 | 60 | 60 | 60 |
| LHSV | 2.5 | 5.0 | 10.0 | 2.5 | 5.0 | 10.0 | 2.5 | 5.0 | 10.0 | 2.5 | 5.0 | 10.0 |
| Isobutylene Conversion, Mol % | 62.1 | 56.2 | 55.7 | 90.6 | 89.1 | — | 99.8 | 97.1 | 93.4 | 100.0 | — | 99.8 |
| Product Composition, LV % | | | | | | | | | | | | |
| Diisobutylene { Dimer I | 67.2 | 68.4 | 66.8 | 57.2 | 55.1 | 55.2 | 37.2 | — | 43.1 | 28.0 | 35.8 | 34.6 |
| Dimer II | 17.7 | 17.8 | 17.9 | 15.9 | 16.3 | 16.0 | 11.5 | — | 14.3 | 9.4 | 11.8 | 11.5 |
| Codimer | 0.9 | 0.9 | 0.7 | 1.0 | 1.6 | 0.9 | 1.8 | — | 2.2 | 2.5 | 1.5 | 2.3 |
| Trimer | 14.1 | 12.9 | 14.3 | 25.8 | 26.9 | 27.9 | 49.5 | — | 40.4 | 60.1 | 50.3 | 51.6 |
| Effluent $\frac{\text{n-Butane}}{\text{Butene-I}}$ Ratio $\frac{\text{Feed}}{1.92}$ | 1.87 | 1.83 | 2.04 | 1.90 | 1.85 | — | 1.80 | 1.83 | 1.86 | 1.61 | — | 1.81 |

The invention claimed is:

1. A process for removing isobutene from a feed stream comprising predominantly $C_4$ hydrocarbons and containing isobutene and n-butene, said isobutene being present in an amount of from about 5 to 60 mole percent comprising:
   (a) contacting said feed stream in liquid phase with a fixed bed cation exchange resin having a granular size of about 0.25 to 1 mm and heat exchange means associated therewith in a reactor at a temperature from 30° to 60° C., said feed stream being fed at a rate of a liquid hourly space velocity from about 2.5 to 12,
   (b) reacting the isobutene to form oligomers thereof having number average molecular weight of $C_{16}$ hydrocarbons or less to form a product stream comprising said $C_4$ hydrocarbons and oligomers and having a substantially lower amount of isobutene than said feed stream, the principal product being the dimer of isobutene, and
   (c) removing said product stream from said reactor.

2. The process according to claim 1 wherein said product stream is fractionated to recover an overhead $C_4$ fraction having an isobutene content substantially lower than said feed stream and a bottoms fraction consisting essentially of said oligomers.

3. The process according to claim 1 wherein said reactor comprises one or more small diameter tubes containing said resin surrounded by said heat exchange medium.

4. The process according to claim 1 wherein said feed stream is fed to the reactor at a pressure in the range of about 35 to 300 psig.

5. The process according to claim 1 wherein said resin is in the form of granular particles having a surface area of 20 to 600 square meters per grams.

6. The process according to claim 3 wherein said tubes are from ½ inch to 2 inches outside diameter.

7. The process according to claim 6 wherein said heat exchange medium is water.

8. The process according to claim 1 wherein the temperature is in the range of 40° to 60° C.

9. The process according to claim 1 wherein the temperature is in the range of 30° to 40° C.

10. The process according to claim 1 wherein the oligomer comprises diisobutene.

11. The process according to claim 2 wherein said isobutene comprises less than 0.2 mole percent of said product stream.

12. A process according to claim 11 wherein said product stream contains at least 50 mole percent of the butene-1 of said feed stream.

13. The process according to claim 12 wherein said product stream contains at least 80 mole percent of the butene-1 of said feed stream.

* * * * *